United States Patent [19]

Kubas

[11] 4,412,613
[45] Nov. 1, 1983

[54] MICROSURGICAL FOAM NEEDLE CONTROL PACKAGE

[75] Inventor: Robert J. Kubas, Ridgefield, Conn.

[73] Assignee: American Cyanamid Company, Stamford, Conn.

[21] Appl. No.: 311,857

[22] Filed: Oct. 19, 1981

Related U.S. Application Data

[63] Continuation-in-part of Ser. No. 215,598, Dec. 12, 1980.

[51] Int. Cl.³ .............................................. A61L 17/02
[52] U.S. Cl. .................................... 206/63.3; 206/459
[58] Field of Search ....................... 206/63.3, 380, 476, 206/408, 472, 491–492, 459; 128/335.5

[56] References Cited

U.S. PATENT DOCUMENTS

| 185,977 | 1/1877 | Smith | 206/214 |
| 233,203 | 10/1880 | Cushman | 206/214 |
| 3,014,582 | 12/1961 | McGrawe | 206/380 |
| 3,759,376 | 9/1973 | Lisowski | 206/63.3 |
| 3,951,261 | 4/1976 | Mandel et al. | 206/380 |
| 4,089,410 | 5/1978 | Bolanowski et al. | 206/63.3 |
| 4,142,628 | 3/1979 | Marocco et al. | 206/63.3 |
| 4,215,777 | 8/1980 | Strickland | 206/63.3 |

Primary Examiner—Joseph Man-Fu Moy
Attorney, Agent, or Firm—Charles F. Costello, Jr.

[57] ABSTRACT

An improved direct dispensing surgical suture package has been invented. The package comprises a center panel; a foam receptacle affixed to said panel; a single-armed surgical suture with the needle engaged in the receptacle; and at least a first flap adjacent and placed onto said panel allowing said receptacle to be visible. The improvement comprises a grid on the exterior package surface, whereby said suture can be dispensed from said package by disengaging and then pulling said needle, and said suture can be oriented and measured by placing it on said grid.

5 Claims, 7 Drawing Figures

4,412,613

MICROSURGICAL FOAM NEEDLE CONTROL PACKAGE

RELATED TO OTHER APPLICATIONS

This is a continuation-in-part application of U.S. Ser. No. 215,598 filed Dec. 12, 1980.

SUMMARY OF THE INVENTION

This invention relates to packaging for a surgical needled suture, and, more particularly, to packaging devices that serve to protect and yet facilitate manipulation and removal of the surgical needled suture.

To reduce the time of operative procedures and to permit surgeons to utilize their skills more effectively, it has become common practice to package surgical tools and appliances so that they are readily accessible to operating room personnel. In addition to using packaging techniques that permit the operating room nurse and the surgeon to manipulate the various surgical devices, the devices are packaged in a sterile environment, so that they are immediately available for use.

In conformance, it has become common practice to package and store surgical needles and sutures in sterile packages. These packages are designed to permit sterilizing the contents, and storing surgical needles and sutures in sterile packages.

The suture packages are designed to permit sterilizing the contents and maintaining the contents in a sterile condition until they are removed for use.

This invention is concerned with a holding device for mounting a suture that protects the point of the needle, acts as a holding device to permit manipulation of the suture, and forms a support on which the suture is organized to avoid tangles, snags or permanent deformation, yet allows rapid removal of the suture without the need for manipulating the holder.

An improved direct dispensing surgical suture package has been invented. The package comprises a center panel; a foam receptacle affixed to said panel; a single-armed surgical suture with the needle engaged in the receptacle; and at least a first flap adjacent and placed onto said panel allowing said receptacle to be visible. The improvement comprises a grid on the exterior package surface, whereby said suture can be dispensed from said package by disengaging and then pulling said needle, and said suture can be oriented and measured by placing it on said grid.

Other embodiments of the improved suture package have a second flap adjacent said panel and said first flap, said second flap placed onto said first flap; a third flap opposite said first flap, said third flap folded onto said second flap and partially onto said first flap; a slit on said first flap to contain a portion of a distal edge of said third flap; and a marking on said grid to show the distance between two parallel lines.

Another embodiment of the improved suture package is a folder containing a center panel and a plurality of flaps, at least two adjacent flaps of said folder being folded to form a pocket, a suture package described above placed into said said pocket and the remaining flaps of said folder being folded. The package can be dispensed from said folder, said suture can be dispensed from said package by disengaging and then pulling said needle, and said suture can be oriented and measured by placing it on said grid.

DESCRIPTION OF THE INVENTION

Figure 1:
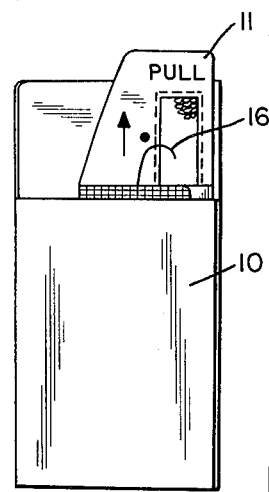
FIG. 1 is a front view of a suture package of this invention.

FIG. 1 describes the preferred absorbable suture package for microsurgical use. The package can be contained in an interior and then in an exterior sealed envelope. An example of an interior and an exterior envelope are described in U.S. Pat. No. 4,089,410, FIGS. 2 and 1, respectively, which are incorporated by reference. A description of how to make the interior envelope is described in U.S. Pat. No. 4,135,622 which is also incorporated by reference. A description of how to make the exterior envelope is described above in conjunction with U.S. Pat. No. 4,089,410 FIG. 1.

Referring to FIG. 1, the absorbable suture package contains a folder 10 and a suture holder 11. The folder 10 wraps around the suture holder to provide tear resistance to the suture holder. The height of the holder 11 is greater than the height of the front portion of the folder 10 to allow the needle 16 to be dispensed.

Referring to FIGS. 1 to 4, an optional embodiment is the word "PULL" and/or an arrow affixed to the upper portion of the holder 11 to indicate the direction for dispensing it from the folder 10. Another optional embodiment is a dot adjacent the butt end of the needle 16 to assist the user in locating the needle in the receptacle 15. Finally, the preferred receptacle 15 is shown in partial view. The needle 16 is therefore shown as being visible. It is to be understood however that the needle 16 is placed into and not on the receptacle 15.

Figure 2:
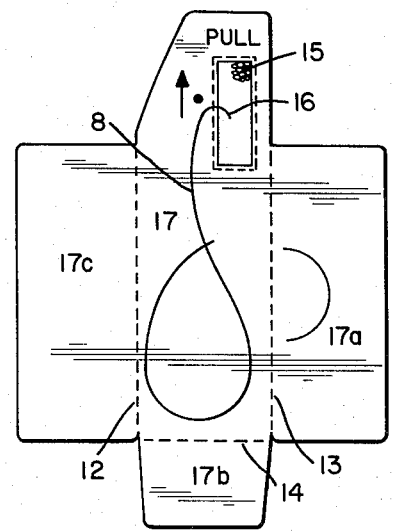
FIG. 2 is a front view of the unfolded holder of FIG. 1.

FIG. 2 describes the suture holder after it has been removed from the exterior and interior envelopes, the folder 10, and then opened along score lines 12, 13 and 14 to show construction and suture configurations. It is to be understood that single or double score lines separating the respective holder panels are within the scope of this invention. The needle 16 is held in place by insertion into the receptacle 15. Preferably, the receptacle is manufactured from a commercially available polypropylene foam. A double backed adhesive can be used to affix the receptacle 15 to the suture holder 11.

The suture 8 is loaded onto the center panel 17. Any loading configuration may be used provided the dispensing of the suture from the holder is without tangling.

The suture package of this invention can be direct dispensing. That is, the suture holder 11 does not have to be unfolded or removed from the interior envelope or from the folder 10 during use. Preferably, however, the suture holder 11 is removed from the folder 10.

The absorbable suture holder 11 can be used by pulling open the exterior envelope. The interior envelope is then projected onto a sterile field. The interior envelope is then opened by a diagonal tear, exposing the needle 16 in the receptacle 15. The user can then dispense the suture 8 by disengaging the needle 16 from the receptacle 15 and then pulling it until the suture is removed from the package.

Figure 3:
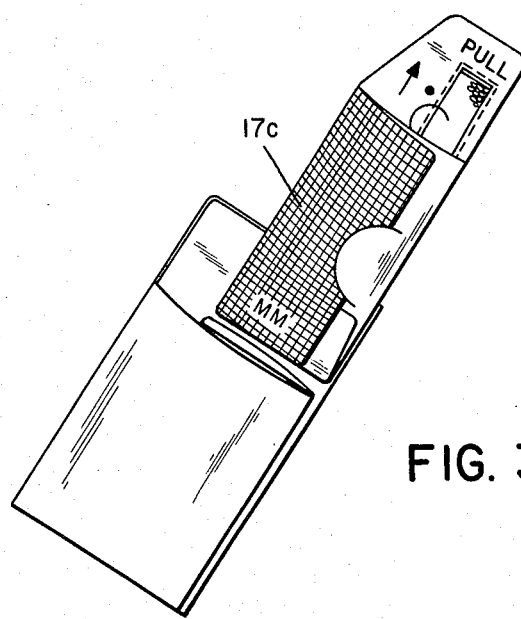
FIG. 3 is a perspective view showing the folded holder of FIG. 2 being removed from the folder of FIG. 1.

Alternatively, referring to FIG. 3, the holder 11 can be removed from the folder 10. The user can then dispense the suture 8 from the holder 11 as described above. A grid on the exterior surface of the panel 17c can be used, for example, to orient and/or to measure the suture 8. A marking, for example "mm", can be used to show the actual distance between two parallel lines of said grid.

Figure 4:
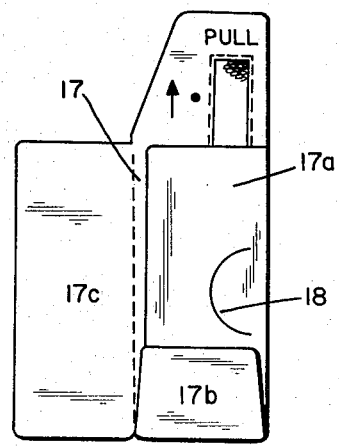
FIG. 4 is a front view showing the folding sequence of the holder of FIG. 2.

FIG. 4 describes the folding sequence of the holder of FIG. 2. Specifically, flap 17a is folded on score line 13 and placed onto center panel 17. Flap 17b is folded onto flap 17a. Flap 17b aids in containing the suture in the suture holder during loading and/or transporting. Flap 17c is then placed onto flap 17b and partially onto flap 17a. Slit 18a on flap 17a is used to contain an edge portion of flap 17c.

Figure 5:
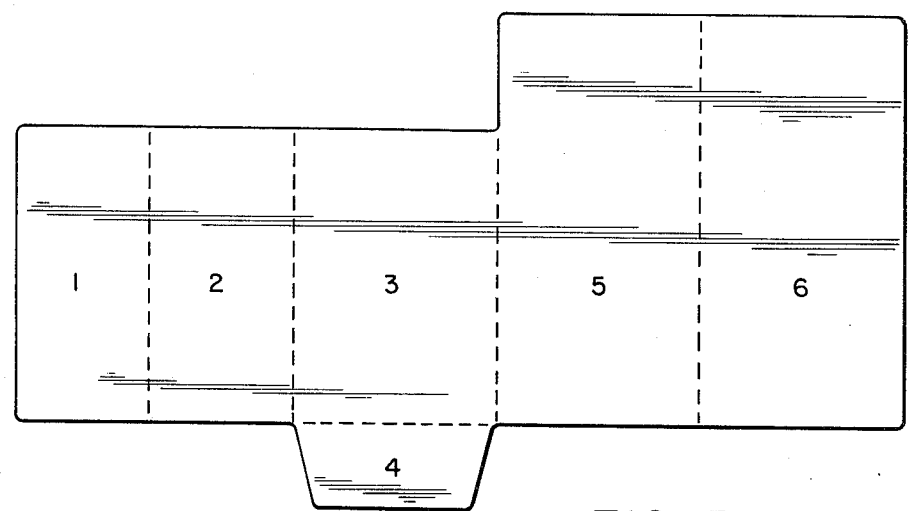
FIGS. 5 to 7 are front views showing the folding sequence of the folder of FIGS. 1 and 3.
Figure 6:
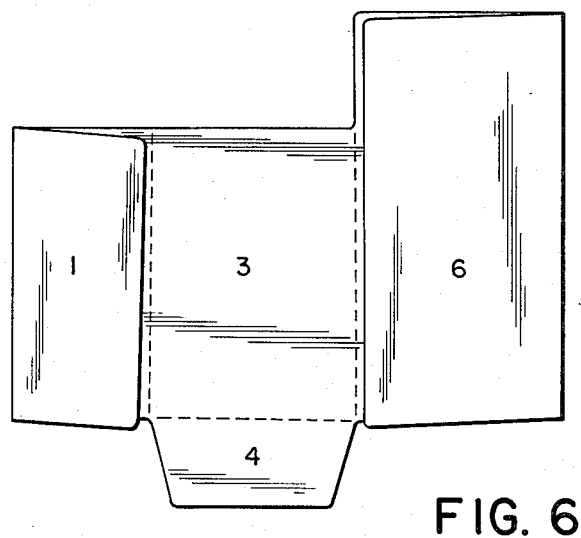
Figure 7:
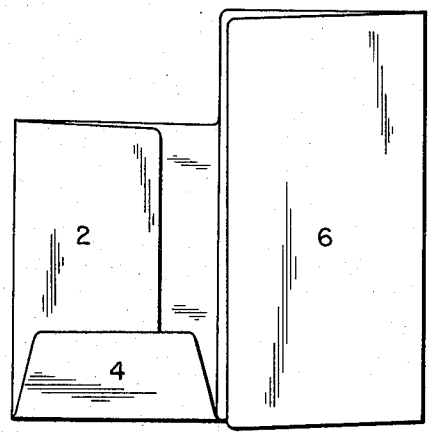

FIG. 5 describes the folder after it has been removed from the exterior and interior envelopes and opened. It is to be understood that single or double score lines separating the respective folder panels can be within the scope of this invention. FIGS. 6 and 7 describe the folding sequence of the suture folder of FIG. 5.

Referring to FIGS. 6 and 7, flap 1 is folded onto flap 2. Flap 1 is then folded onto the center panel 3. Flap 4 is folded onto flap 2. Flap 6 is then folded onto flap 5. Flap 6 is then folded onto flap 4 and partially onto flap 3.

FIG. 3 describes a method of loading the suture holder 11 into the folder 10. As described above, FIG. 11 also describes a method of removing the folder 10 from the holder 11.

An alternative method of loading the holder 11 into the folder 10 is described in conjunction with FIGS. 6 and 7. The suture holder 11 can be placed in the pocket of the partially formed folder 10 between flaps 1 and 2. In this alternative method of loading, center panel 17 can be placed onto flap 1 of the folder 10. The folder 10 can then be completely assembled as described in FIGS. 6 and 7.

I claim:

1. A direct dispensing surgical suture package comprising a center panel; a foam receptacle affixed to said panel; a single-armed surgical suture with the needle engaged in the receptacle; and at least a first flap adjacent and placed onto said panel allowing said receptacle to be visible, the improvement comprising a folder containing a second center panel and a plurality of side flaps, at least two adjacent side flaps of said folder being folded to form a pocket, said suture package placed into said pocket and the remaining side flaps of said folder being folded, whereby said package can be dispensed from said folder, and a grid on the exterior suture package surface whereby said suture can be dispensed from said package by disengaging and then pulling said needle, and said suture can be oriented and measured by placing it on said grid.

2. A suture package of claim 1 having a second flap adjacent said panel and said first flap, said second flap placed onto said first flap.

3. A suture package of claim 2 having a third flap opposite said first flap, said third flap folded onto said second flap and partially onto said first flap.

4. A suture package of claim 3 having a slit on said first flap to contain a portion of a distal edge of said third flap.

5. A suture package of claim 1 or 2 or 3 or 4 having a marking on said grid to show the distance between two parallel lines.

* * * * *